United States Patent [19]

McElligott

[11] Patent Number: 4,704,489

[45] Date of Patent: Nov. 3, 1987

[54] ISOMERIZATION OF LINALYL HALIDES WITH ALCOHOLS

[75] Inventor: Lois T. McElligott, Abington, Pa.

[73] Assignee: Union Camp Corporation, Wayne, N.J.

[21] Appl. No.: 749,923

[22] Filed: Jun. 28, 1985

Related U.S. Application Data

[63] Continuation-in-part of Ser. No. 560,139, Dec. 12, 1983, abandoned.

[51] Int. Cl.⁴ ............................................. C07C 17/24
[52] U.S. Cl. .................................................... 570/236
[58] Field of Search ........................................ 570/236

[56] References Cited

U.S. PATENT DOCUMENTS

| | | | |
|---|---|---|---|
| 2,104,789 | 1/1938 | Carothers | 570/236 |
| 2,871,271 | 12/1986 | Booth | 570/231 |
| 3,061,653 | 10/1962 | Stewart | 570/236 |
| 3,515,760 | 6/1970 | Weld | 570/236 |
| 3,927,130 | 12/1975 | Kadowaki et al. | 570/236 |

FOREIGN PATENT DOCUMENTS 160206  12/1975  Japan .................................. 570/236

*Primary Examiner*—J. E. Evans
*Assistant Examiner*—Joseph A. Boska
*Attorney, Agent, or Firm*—Kane, Dalsimer, Sullivan, Kurucz, Levy, Eisele and Richard

[57] ABSTRACT

A method for the isomerization of linalyl halides is disclosed, improved by the presence of an alcohol. The improved method of the invention requires less energy for completion of the isomerization and shortens the isomerization times.

7 Claims, No Drawings

ISOMERIZATION OF LINALYL HALIDES WITH ALCOHOLS

CROSS-REFERENCE TO RELATED APPLICATION

This application is a continuation-in-part of copending application Ser. No. 560,139 filed Dec. 12, 1983, abandoned.

BACKGROUND OF THE INVENTION

1. Field of the Invention

The invention relates to the isomerization of linalyl halides.

2. Brief Description of the Prior Art

Representative of the prior art is the description given in the U.S. Pat. No. 2,104,789 to Carothers. The prior art class deals mainly with simply compounds such as the chloro and dichloro butenes. Generally, the reactions are carried out in the presence of water, methanol, ethanol, or acetic acid. In spite of the availability of these known methods of isomerizing allylic halides, there has remained a need for processes operating at low temperature and effective for more complex halides which are heat-sensitive and are prone to solvolysis in the presence of water, methanol, and acetic acid. The method of the present invention is such an improvement over the prior art, requiring relatively low temperatures and short isomerization times and employing a relatively inexpensive catalyst which can be recovered and reused many times, and which does not promote solvolysis.

SUMMARY OF THE PRESENT INVENTION

The present invention comprises a method for isomerizing linalyl halides to their allylic isomers, neryl and geranyl halides, comprising isomerizing linalyl halide in the presence of a catalytic proportion of a copper-containing catalyst and further comprising carrying out the isomerization at a temper-ature below 25° C. in the presence of a catalytic proportion of an anhydrous hydrogen halide and a primary or secondary alcohol containing at least three carbon atoms.

The term "halide" as used herein is embracive of chloride, bromide, and iodide.

DETAILED DESCRIPTION OF THE PREFERRED EMBODIMENTS OF THE PRESENT INVENTION

The method of the present invention may be employed to isomerize linalyl chloride to the geranyl and neryl chlorides according to the schematic formulae:

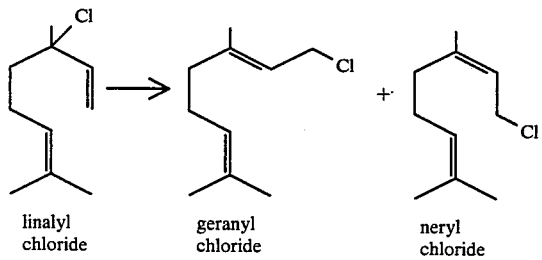

linalyl chloride    geranyl chloride    neryl chloride

The method of the invention is an improvement over isomerizations carried out in the presence of hydrogen halides and copper catalysts alone. Representative of hydrogen halides so employed are hydrogen chloride and hydrogen bromide. In general, catalytic proportions of the hydrogen halide are used. Catalytic proportions are generally within the range of from about 0.01 to 5 percent by weight of the starting halides, preferably 0.1 to 1.0 percent.

The copper-containing catalysts employed may be any copper compound having a valency of 2 or less, including metallic copper. Any copper compound covertible to the halide, such as the bromide, iodide, or chloride, under conditions of the reaction may also be used. Representative of copper catalysts advantageously employed are the chloride, bromide, carbonate, oxide, acetate, formate, sulfate, and like derivative cupric and cuprous compounds. Preferred as the copper catalyst in the improved process of the invention is cuprous chloride. Catalytic proportions of the copper catalyst are generally within the weight range of from about 0.01 to 2 percent of the allylic halide starting compound, preferably about 0.5 percent.

A wide range of primary and secondary alcohols may be employed to catalyze the isomerization of allylic halides, according to the method of the invention. Advantageously, the alcohol selected is a fluid under conditions of the process of the invention and is inert to reaction with the isomerization reaction mixture components. Representative of such alcohols are:

n-hexanol,
n-octanol,
n-decanol,
n-tetradecanol,
isopropanol,
isobutanol,
3-pentanol,
cyclohexanol,
2-ethylhexanol, and the like. Preferred alcohols are those of the general formula:

$$R-OH \qquad (I)$$

wherein R represents alkyl or aralkyl.

The term "alkyl" as used herein means the monovalent moiety obtained upon removal of a hydrogen atom from a parent straight-chain, branched-chain, or cyclic alkane. Representative of alkyl are alkyl of 3 to 25 carbon atoms, inclusive, such as propyl, butyl, pentyl, hexyl, cyclohexyl, heptyl, octyl, nonyl, undecyl, decyl, dodecyl, octadecyl, nonodecyl, eicosyl, heneicosyl, docosyl, tricosyl, tetracosyl, pentacosyl, and the isomeric forms thereof.

The term "aralkyl" as used herein means alkyl as defined above wherein a hydrogen atom has been replaced with a monovalent moiety obtained upon removal of a hydrogen atom from an aromatic hydrocarbon. Representative of aralkyl are aralkyl of 7 to 25 carbon atoms, inclusive, such as benzyl, phenethyl, phenpropyl, phenbutyl, phenhexyl, napthoctyl, and the like. Preferably, the R moiety will contain from 4 to 25 carbon atoms, inclusive, most preferably 6 to 10 carbon atoms, inclusive.

It will be appreciated that under specific conditions of operating the process of the invention, certain of the above-described alcohols of the formula (I) given above have advantages over other compounds of the same general formula. Selection of a particular alcohol for use under specific process conditions for optimum yields may be made by trial and error techniques.

The alcohol is used in a proportion to isomerize at least some of the allylic halide according to the method of the invention. Such a proportion is generally within the range of from about 0.01 to 10 percent by weight of the halide charge, preferably 0.1 to 5 percent. Used in such small amounts, the alcohol does not appreciably change the polarity of the medium so as to promote solvolysis of the chlorides. Optimum proportions will depend to some extent upon the alcohol selected and may be determined by trial and error technique. Generally the preferred molar ratio of alcohol to copper catalyst is from 0.01 to 5.0.

The method of the invention may be carried out by admixing the starting linayl halide with the hydrogen halide, copper catalyst, and alcohol in a suitable vessel for a sufficient period of time to effect the desired isomerization. We have found that in isomerization of linalyl chloride the preferred minimum total residence time is within the range of from 0.1 to 10 hours and most preferably 0.5 to 8 hours under preferred operating temperatures.

Although the method of the invention may be carried out under a range of operating temperatures, i.e., within the range of from about −10° C. to 25° C., it is preferred to do so at a temperature of from 0° C. to 20° C. and most preferably about 10° C.

The method of the invention is not dependent upon pressure, and may be carried out at atmospheric, subatmospheric, or super-atmospheric pressures.

Progress of the isomerization may be monitored by conventional analytical techniques. When it has been determined that isomerization occurred to a maximum desired point, the product mixture may be passed from the reaction apparatus. The alcohol catalyst may be recovered by conventional procedures, for example, by distillation. The recovered alcohol can be reused in the method of the invention.

The following examples describe the manner and process of making and using the invention and set forth the best mode contemplated by the inventors for carrying out the invention, but are not to be construed as limiting. All parts given are by weight unless otherwise indicated.

EXAMPLES

Examples 1-5

To 8.0 g of myrcene hydrochlorides (typically consisting of 51 parts linalyl chloride, 11 parts neryl chloride, 8 parts geranyl chloride, 8 parts alpha-terpinyl chloride, and 22 parts hydrocarbons) there is added 0.03 g of cuprous chloride, an alcohol compound in an amount indicated in Table 1 below, and 0.02 g hydrogen chloride gas. The mixture is stirred at 10° C. for 8 hours. Samples of the reaction mixture are withdrawn at 2 hour intervals, neutralized with aqueous sodium hydroxide, and analyzed by gas chromatography. The analytical results are shown in Table 1 below, which also shows the alcohol employed. Linalyl, neryl, and geranyl chlorides are abbreviated LCl, NCl and GCl, respectively.

TABLE 1

| Example No. | Alcohol and Amount Used | Amount of Time To Reduce LCl Content By One-Half (hrs.) | GCl:NCl Ratio After 8 Hours |
|---|---|---|---|
| 1 | none (control) | 5-6 | 1.4 |
| 2 | n-hexanol, 0.03 g | 1 | 1.5 |
| 3 | cyclohexanol, 0.03 g | 1 | 1.5 |
| 4 | n-decanol, 0.04 g | 1.5 | 1.5 |
| 5 | 3-pentanol, 0.02 g | 1.5 | 1.5 |

What is claimed:

1. A method of isomerizing linalyl halide to neryl and geranyl halides comprising isomerizing the linalyl halide in the presence of a catalytic portion of a copper-containing catalyst, and further comprising carrying out the isomerization at a temperature of from about −10° C. to 25° C. in the presence of a catalytic proportion of an anhydrous hydrogen halide and from about 0.01 to 10 percent by weight of the linalyl halide of a primary or secondary alcohol containing at least three carbon atoms.

2. The process of claim 1 wherein the alcohol is selected from the group of the formula:

R—OH wherein R is selected from the group consisting of alkyl having 3 to 25 carbon atoms, inclusive, and aralkyl having 7 to 25 carbon atoms, inclusive.

3. The process of claim 2 wherein the alcohol is selected from the group consisting of n-hexanol, cyclohexanol, n-octanol, n-decanol, 3-pentanol, and isoamyl alcohol.

4. The process of claim 1 wherein the copper-containing catalyst is cuprous chloride.

5. The process of claim 4 wherein the catalytic proportion of copper catalyst is within the weight range of about 0.01 to about 2.0 percent linalyl halide.

6. The process of claim 1 wherein the molar ratio of alcohol to copper catalyst is about 0.01 to about 5.0.

7. The process of claim 1 wherein the isomerization is carried out for a period of about 0.1 to about 10.0 hours.

* * * * *